(12) United States Patent
Shikata

(10) Patent No.: US 11,510,648 B2
(45) Date of Patent: Nov. 29, 2022

(54) ULTRASONIC DIAGNOSTIC APPARATUS, ULTRASONIC PROBE, AND ULTRASONIC DIAGNOSTIC ASSISTANCE METHOD

(71) Applicant: Canon Medical Systems Corporation, Otawara (JP)

(72) Inventor: Hiroyuki Shikata, Nasushiobara (JP)

(73) Assignee: Canon Medical Systems Corporation, Otawara (JP)

( * ) Notice: Subject to any disclaimer, the term of this patent is extended or adjusted under 35 U.S.C. 154(b) by 287 days.

(21) Appl. No.: 15/878,497

(22) Filed: Jan. 24, 2018

(65) Prior Publication Data

US 2018/0206821 A1 Jul. 26, 2018

(30) Foreign Application Priority Data

Jan. 25, 2017 (JP) .............................. JP2017-011384
Dec. 19, 2017 (JP) .............................. JP2017-242566

(51) Int. Cl.
*A61B 8/00* (2006.01)
*G01S 7/52* (2006.01)
(Continued)

(52) U.S. Cl.
CPC .......... *A61B 8/4494* (2013.01); *A61B 8/5207* (2013.01); *A61B 8/54* (2013.01);
(Continued)

(58) Field of Classification Search
CPC ....... A61B 8/4494; A61B 8/5207; A61B 8/54; A61B 8/4444; A61B 8/488; A61B 8/483;
(Continued)

(56) References Cited

U.S. PATENT DOCUMENTS

| 6,867,720 B1* | 3/2005 | Freeman ............. G01S 7/52028 |
| | | 341/143 |
| 2011/0028846 A1* | 2/2011 | Tsao ................... G01S 15/8927 |
| | | 600/459 |

(Continued)

FOREIGN PATENT DOCUMENTS

| JP | 2010-187833 | 9/2010 |
| JP | 2012-152432 | 8/2012 |
| WO | WO 2017/026278 A1 | 2/2017 |

OTHER PUBLICATIONS

Wang, H., Qiu, Y., Demore, C. E., Gebhardt, S., & Cochran, S. (Sep. 2016). 2-D crossed-electrode transducer arrays for ultrasonic particle manipulation. In 2016 IEEE International Ultrasonics Symposium (IUS) (pp. 1-4). IEEE. (Year: 2016).*

*Primary Examiner* — Christopher Koharski
*Assistant Examiner* — Renee C Langhals
(74) *Attorney, Agent, or Firm* — Oblon, McClelland, Maier & Neustadt, L.L.P.

(57) ABSTRACT

According to one embodiment, an ultrasonic diagnostic apparatus includes an ultrasonic probe and control circuitry. The ultrasonic probe includes a plurality of ultrasonic transducers two-dimensionally arranged along a first arrangement direction and a second arrangement direction. The control circuitry transmits first line delay data and second line delay data to the ultrasonic probe. The ultrasonic probe further comprises setting circuitry configured to set a delay amount for each of the plurality of ultrasonic transducers, by using the transmitted first line delay data and second line delay data.

7 Claims, 12 Drawing Sheets

(51) Int. Cl.
 *G01S 15/89* (2006.01)
 *A61B 8/08* (2006.01)
(52) U.S. Cl.
 CPC .......... *G01S 7/5202* (2013.01); *G01S 7/5208* (2013.01); *G01S 7/52025* (2013.01); *G01S 15/8925* (2013.01); *G01S 15/8927* (2013.01); *A61B 8/4444* (2013.01); *A61B 8/483* (2013.01); *A61B 8/488* (2013.01); *G01S 15/8993* (2013.01)
(58) Field of Classification Search
 CPC .. G01S 7/5208; G01S 7/52025; G01S 7/5202; G01S 15/8925; G01S 15/8927; G01S 15/8993
 USPC ........................................................ 600/459
 See application file for complete search history.

(56) References Cited

U.S. PATENT DOCUMENTS

| | | | |
|---|---|---|---|
| 2012/0179044 A1* | 7/2012 | Chiang | A61B 8/145 600/447 |
| 2012/0310096 A1 | 12/2012 | Hongou et al. | |
| 2013/0310695 A1* | 11/2013 | Hongou | A61B 8/54 600/459 |
| 2015/0301165 A1* | 10/2015 | Rothberg | G01S 7/52019 367/117 |
| 2018/0214123 A1* | 8/2018 | Takano | G01S 7/5202 |

* cited by examiner

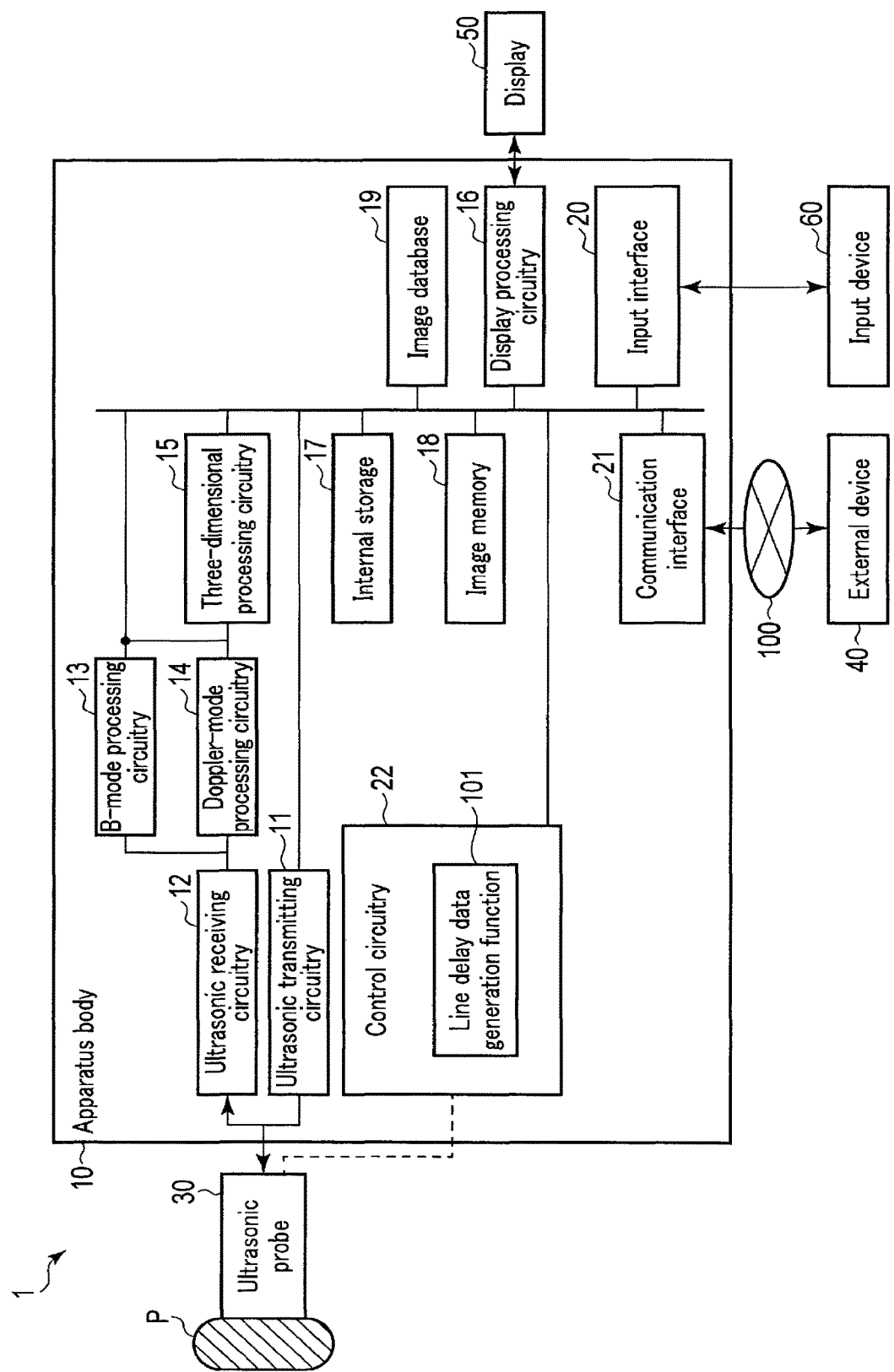
F I G. 1

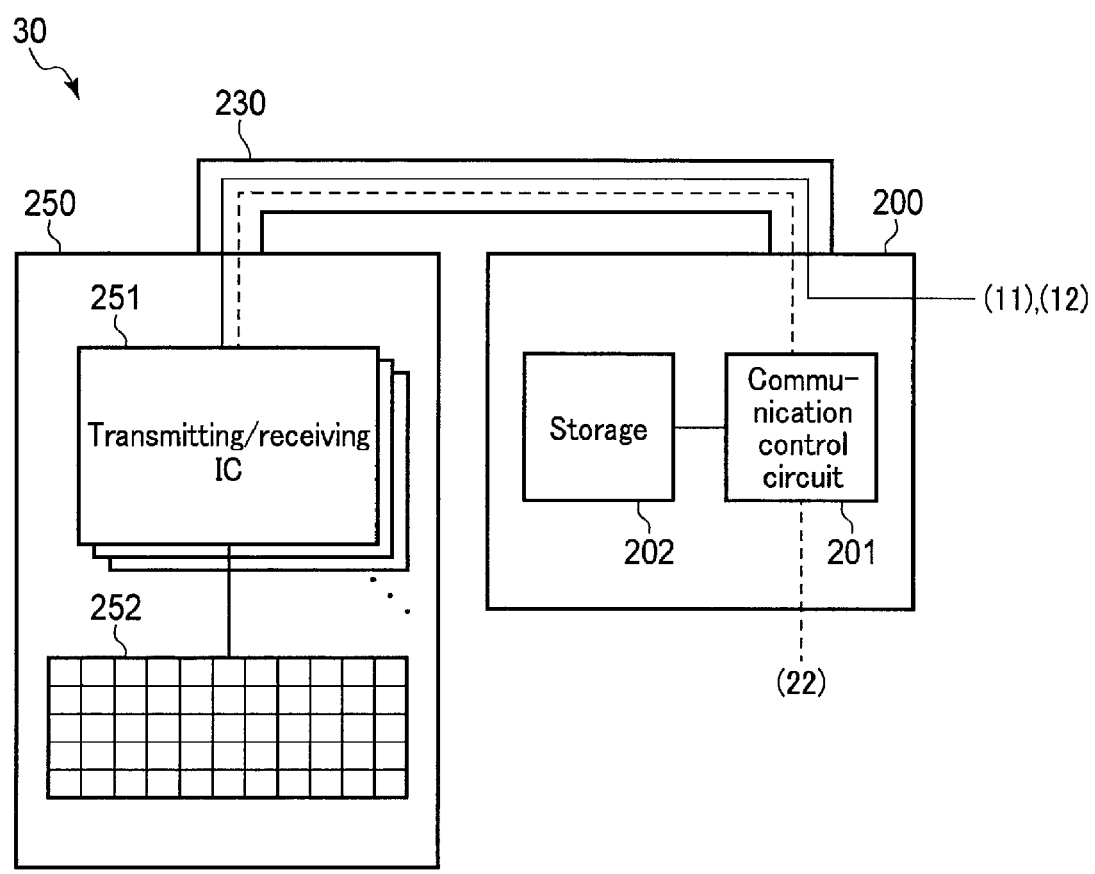
F I G. 2

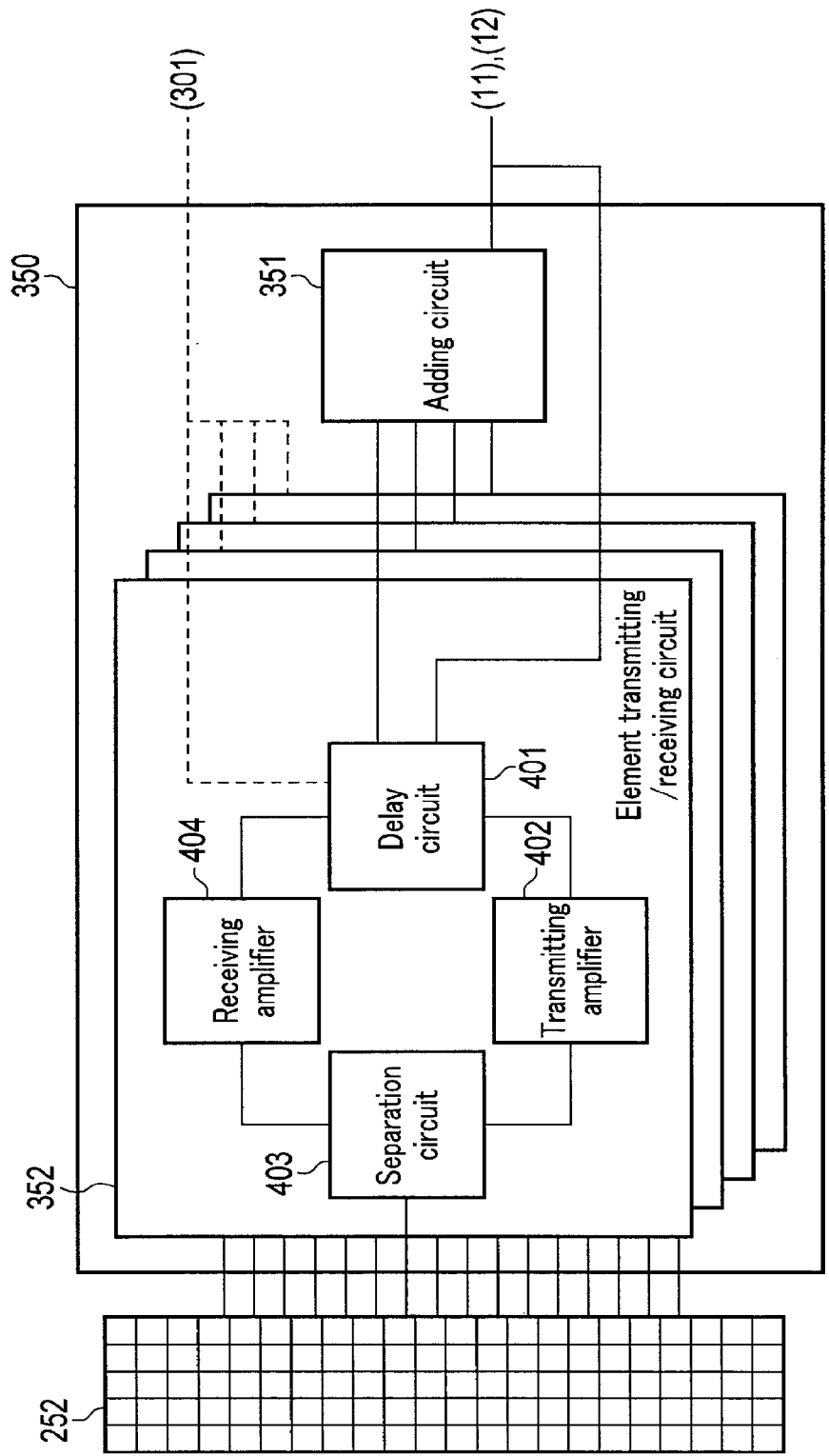
F I G. 4

(b) Present embodiment (a) Conventional technique

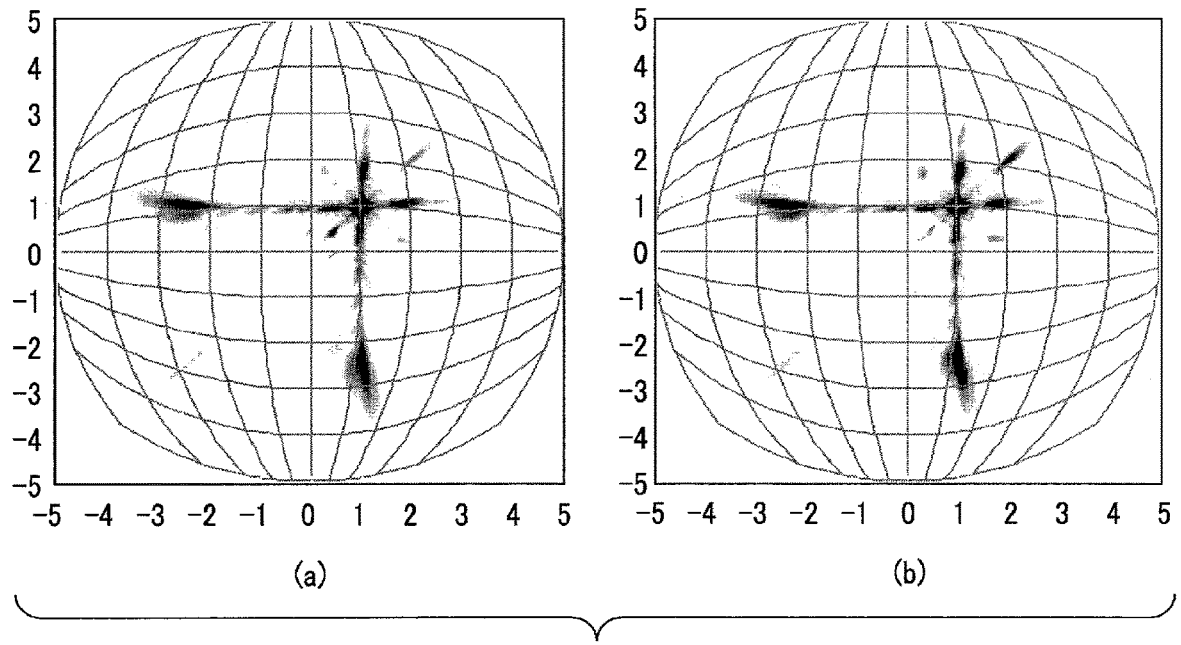
F I G. 10
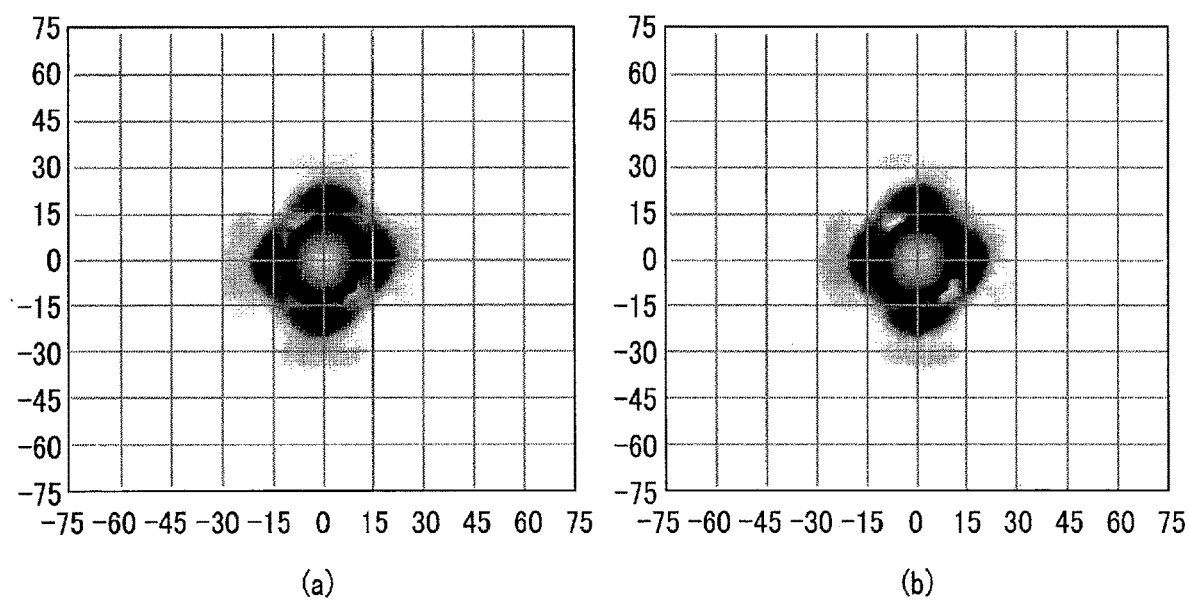
F I G. 11

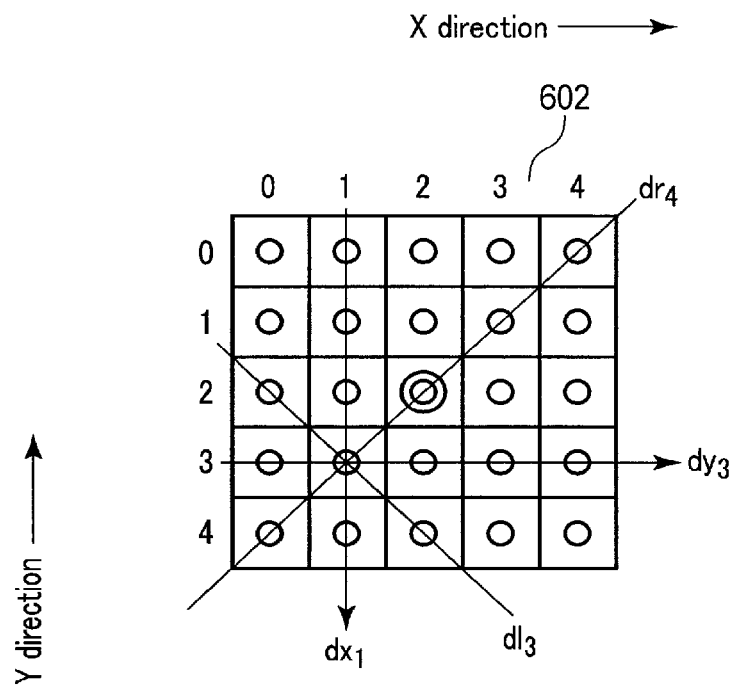
F I G. 13
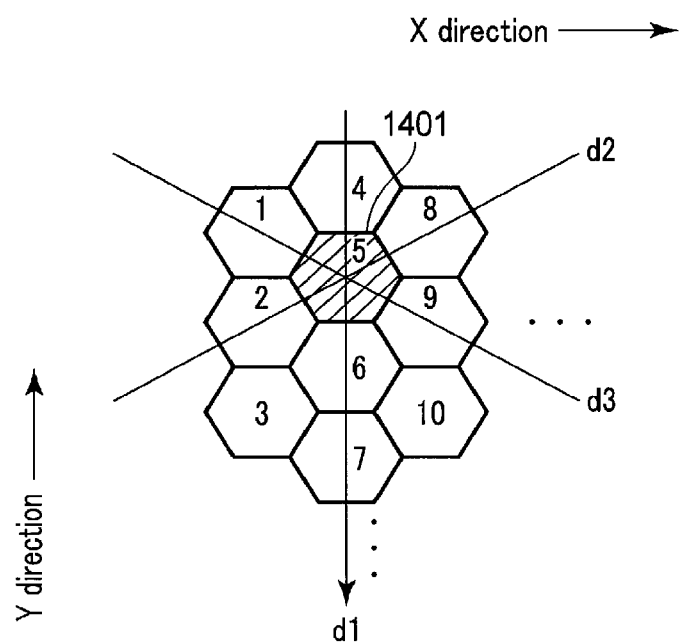
F I G. 14

ULTRASONIC DIAGNOSTIC APPARATUS, ULTRASONIC PROBE, AND ULTRASONIC DIAGNOSTIC ASSISTANCE METHOD

CROSS-REFERENCE TO RELATED APPLICATIONS

This application is based upon and claims the benefit of priority from the prior Japanese Patent Applications No. 2017-011384, filed Jan. 25, 2017, and No. 2017-242566, filed Dec. 19, 2017, the entire contents of all of which are incorporated herein by reference.

FIELD

Embodiments described herein relate generally to an ultrasonic diagnostic apparatus, an ultrasonic probe, and an ultrasonic diagnostic assistance method.

BACKGROUND

An ultrasonic diagnosis apparatus transmits ultrasonic waves to a subject (patient), and receives reflected waves (echo) from the subject to generate an image of the inside of the subject. Recently, mainly two-dimensional array type ultrasonic probes have been used.

The two-dimensional array type probes have a large number of ultrasonic transducers (also referred to as elements) two-dimensionally arranged as a grid, thus it is difficult for the ultrasonic diagnostic apparatus body to directly drive all the elements to control transmission/reception of ultrasonic waves. Therefore, the ultrasonic probe is provided with an IC (ASIC) specific to perform partial delay calculation for each sub-array obtained by dividing the elements.

It is necessary to set delay patterns relating to each element in a sub-array during a blanking time which is a time period from completion of receiving echo signals to transmission of a subsequent ultrasonic wave.

BRIEF DESCRIPTION OF THE DRAWINGS

FIG. 1 is a block diagram of an ultrasonic diagnostic apparatus according to the present embodiment.

FIG. 2 is a block diagram of the configuration of an ultrasonic probe.

FIG. 4 is a block diagram of the configuration of a sub-array unit.

FIG. 10 illustrates a second comparison result between the conventional technique and the processing of the ultrasonic diagnostic apparatus according to the present embodiment.

FIG. 11 shows magnified views of the sound pressure intensity of main beams in FIG. 10.

FIG. 13 is a diagram to explain line delay data according to a modification of the embodiment.

FIG. 14 is a diagram to explain calculation of a delay amount in the case where micromachining ultrasound transducer (MUT) elements are two-dimensionally arranged.

DETAILED DESCRIPTION

Figure 3:
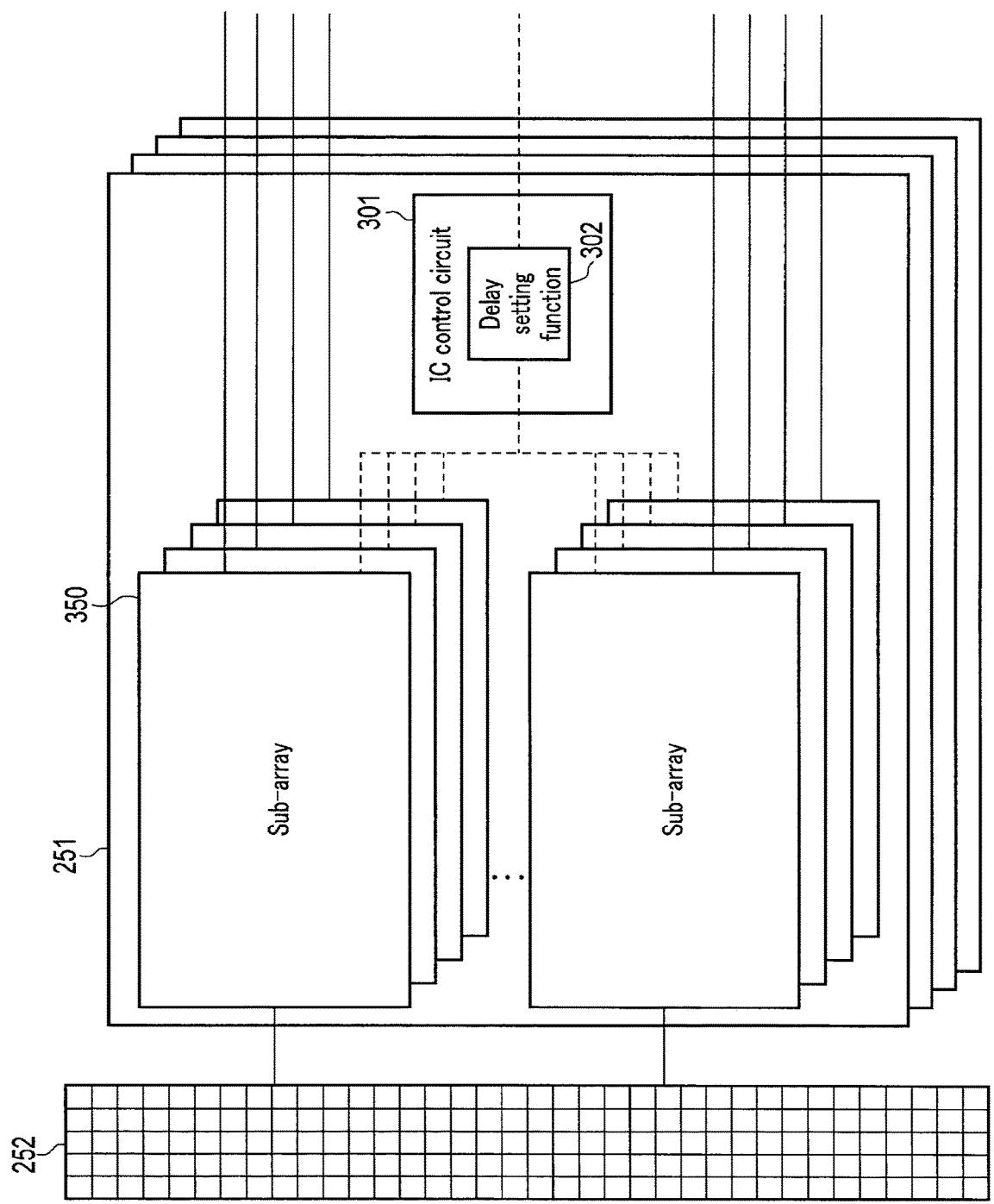
FIG. 3 is a block diagram of the configuration of a transmitting/receiving IC.

When using, for example, the typical sector type of ultrasonic probes, the communication data amount relating to a delay pattern for each element is small. Accordingly, data transmission terminal for ultrasonic transmission can be completed for the blanking time. However, when using large area and large scale two-dimensional array type probes such as linear type probes, the communication data amount relating to a delay pattern for each element becomes several tens of times of that of the sector type of ultrasonic probes, and accordingly, the time to transfer that amount is required. It is necessary to perform high-speed communication or remarkably increase the data transmission lane, in order to transmit data relating to the delay pattern for each element for a shorter time.

However, in order to perform high-speed communication, the circuit scale has to be increased, for example, by increasing a clock frequency of the CPU. In order to increase the data lane, the number of cables has to be increased. Thus, the above options are not considered as realistic solutions.

In general, according to one embodiment, an ultrasonic diagnostic apparatus includes an ultrasonic probe and control circuitry. The ultrasonic probe includes a plurality of ultrasonic transducers two-dimensionally arranged along a first arrangement direction and a second arrangement direction. The control circuitry is configured to transmit first line delay data and second line delay data to the ultrasonic probe, the first line delay data indicating a delay amount for each line of the ultrasonic transducers along the second arrangement direction, the second line delay data indicating a delay amount for each line of the ultrasonic transducers along the first arrangement line. The ultrasonic probe further comprises setting circuitry. The setting circuitry is configured to set a delay amount for each of the plurality of ultrasonic transducers, by using the transmitted first line delay data and second line delay data.

In the following descriptions, an ultrasonic diagnostic apparatus, an ultrasonic probe and an ultrasonic diagnostic assistance method according to the present embodiments will be described with reference to the drawings. In the embodiments described below, elements assigned with the same reference symbols perform the same operations, and redundant descriptions thereof will be omitted as appropriate.

FIRST EMBODIMENT

An ultrasonic diagnostic apparatus according to the present embodiment will be explained with reference to the block diagram of FIG. 1.

FIG. 1 is a block diagram of a configuration example of an ultrasonic diagnostic apparatus 1 according to the present embodiment. As shown in FIG. 1, the ultrasonic diagnostic apparatus 1 includes an apparatus body 10 and an ultrasonic probe 30. The apparatus body 10 is connected to an external device 40 via a network 100. The apparatus body 10 is connected to a display 50 and an input device 60. In the drawings, a solid line represents an analog signal, and a broken line represents a digital signal.

The ultrasonic probe 30 includes a plurality of ultrasonic transducers (also referred to as elements), a matching layer provided to elements, and a backing material that prevents propagation of ultrasonic waves to the rear side of the elements. The ultrasonic probe 30 is detachably connected to the apparatus body 10. The ultrasonic probe 30 will be described later in detail.

The apparatus body 10 shown in FIG. 1 generates an ultrasonic image, based on reflected wave signals received by the ultrasonic probe 30. As shown in FIG. 1, the apparatus body 10 includes ultrasonic transmitting circuitry 11, ultrasonic receiving circuitry 12, B-mode processing circuitry 13, Doppler-mode processing circuitry 14, three-dimensional processing circuitry 15, display processing circuitry 16, an internal storage 17, an image memory 18 (cine memory), an image database 19, input interface circuitry 20, communication interface circuitry 21, and control circuitry 22.

The ultrasonic transmitting circuitry 11 is a processor that supplies driving signals to the ultrasonic probe 30. The ultrasonic transmitting circuitry 11 is implemented, for example, by trigger generating circuitry, delay circuitry, and pulser circuitry, etc. The trigger generating circuitry repeatedly generates rate pulses for forming transmission ultrasonic waves at a predetermined rate frequency. The delay circuitry converges ultrasonic waves generated from the ultrasonic probe 30 as a beam, and applies, to each rate pulse generated by the trigger generating circuitry, a transmission delay time for each element required for determining a transmission directivity. The pulser circuitry supplies driving signals (a driving pulse) to the ultrasonic probe 30 at a timing based on the rate pulse. By changing the transmission delay time to be applied to each rate pulse from the delay circuitry, the transmission direction from the element surface can be discretionarily adjusted.

The ultrasonic receiving circuitry 12 is a processor that executes various processes on reflected wave signals received by the ultrasonic probe 30 to generate a receive signal. The ultrasonic receiving circuitry 12 is implemented, for example, by amplification circuitry, an A/D converter, reception delay circuitry, and an adder, etc. The amplification circuitry executes a gain correction process for each channel by amplifying reflected wave signals received by the ultrasonic probe 30. The A/D converter converts the gain-corrected reflected wave signals to digital signals. The reception delay circuitry delays input of the digital signals to the adder by a reception delay time required for determining a reception directivity. The adder adds a plurality of digital signals in which the reception delay time has been applied. After the addition process of the adder, receive signals are generated in which a reflected component from a direction corresponding to the reception directivity is emphasized.

The B-mode processing circuitry 13 is a processor that generates B-mode data, based on the receive signals received from the ultrasonic receiving circuitry 12. The B-mode processing circuitry 13 executes an envelope detection process and a logarithmic amplification process, etc. on the receive signals received from the ultrasonic receiving circuitry 12, and generates data (B-mode data) in which the signal intensity is expressed by the brightness intensity. The generated B-mode data is stored in a RAW data memory (not shown in the drawings) as B-mode RAW data on an ultrasonic scanning line. The B-mode RAW data may be stored in the internal storage 17 described later.

The Doppler-mode processing circuitry 14 is a processor that generates a Doppler waveform and Doppler data, based on the receive signals received from the ultrasonic receiving circuitry 12. The Doppler-mode processing circuitry 14 extracts a blood flow signal from the receive signal, generates a Doppler waveform from the extracted blood flow signal, and generates data (Doppler data) in which information, such as a mean velocity, dispersion, power, etc. is extracted from the blood flow signal with respect to multiple points.

The three-dimensional processing circuitry 15 is a processor that can generate two-dimensional image data or three-dimensional image data (also referred to as volume data), based on the data generated by the B-mode processing circuitry 13 and the Doppler-mode processing circuitry 14. The three-dimensional processing circuitry 15 performs RAW-pixel conversion to generate two-dimensional image data consisting of pixels.

In addition, the three-dimensional processing circuitry 15 performs, to B-mode RAW data stored in a RAW data memory, RAW-voxel conversion which includes an interpolation process taking spatial position information into consideration to generate volume data consisting of voxels in a desired range. The three-dimensional processing circuitry 15 generates rendering image data by performing a rendering process to the generated volume data. The B-mode RAW data, the two-dimensional image data, the volume data, and the rendering image data are generically referred to as ultrasonic data.

The display processing circuitry 16 executes various processes, such as dynamic range, brightness, contrast and y curve corrections, and RGB conversion, etc. to image data generated in the three-dimensional processing circuitry 15, in order to convert the image data to a video signal. The display processing circuitry 16 directs the display 50 to display the video signal. The display processing circuitry 16 may generate a user interface (Graphical User Interface: GUI) through which an operator inputs various instructions by the input interface circuitry 20, and directs the display 50 to display the GUI. The display 50 may adopt, for example, a CRT display, a liquid crystal display, an organic EL display, an LED display, a plasma display, or any other displays known in this technical field.

The internal storage 17 includes, for example, a storage medium which is readable by a processor, such as a magnetic or optical storage medium, or a semiconductor memory, etc. The internal storage 17 stores a control program relating to a delay amount setting method, a control program for implementing ultrasonic transmission/reception, a control program for executing an image process, and a control program for executing a display process, according to the present embodiment. In addition, the internal storage 17 stores diagnosis information (e.g., patient ID, doctor's findings, etc.), a diagnosis protocol, a body mark generation program, and data such as a conversion table for presetting a range of color data for use in imaging, with respect to each of regions of diagnosis. The internal storage 17 may store anatomical illustrations, for example, an atlas, relating to the structures of internal organs in the body.

In addition, the internal storage 17 stores two-dimensional image data, volume data, and rendering image data generated by the three-dimensional processing circuitry 15, in accordance with a storing operation input via the input interface circuitry 20. In accordance with a storing operation input via the input interface circuitry 20, the internal storage 17 may store two-dimensional image data, volume data, and rendering image data generated by the three-dimensional processing circuitry 15, along with an operation order and an operation time. The internal storage 17 can transfer the stored data to an external device through the communication interface circuitry 21.

The image memory 18 includes, for example, a storage medium which is readable by a processor, such as a magnetic or optical storage medium, or a semiconductor memory. The image memory 18 stores image data corresponding to a plurality of frames immediately before a freeze operation input through the input interface circuitry 20. The image data stored in the image memory 18 is successively displayed (cine-displayed), for example.

The image database 19 stores image data transferred from the external device 40. For example, the image database 19 acquires and stores past medical image data relating to a particular patient obtained by the past diagnosis and stored in the external device 40. The past medical image data includes ultrasonic image data, Computed Tomography (CT) image data, MR image data, Positron Emission Tomography (PET)-CT image data, PET-MR image data, and X-ray image data.

The image database 19 may store desired image data by reading image data stored in a storage medium such as an MO, a CD-R and a DVD.

The input interface circuitry 20 receives various instructions from an operator through the input device 60. The input device 60 is, for example, a mouse, a keyboard, a panel switch, a slider switch, a trackball, a rotary encoder, an operation panel, and a touch command screen (TCS). The input interface circuitry 20 is connected to the control circuitry 22, for example, via a bus. The input interface circuitry 20 converts an operation instruction input by the operator into electric signals, and outputs the electric signals to the control circuitry 22. In the present embodiments, the input interface circuitry 20 is not limited to interface circuitry which is connected to physical operation components such as a mouse, a keyboard, etc. The input interface circuitry 20 may include processing circuitry of electric signals which receives, as radio signals, electric signals corresponding to an operation instruction input from an external input device independent from the ultrasonic diagnostic apparatus 1, and outputs the electric signals to the control circuitry 22. The external input device may be, for example, an external input device that is capable of transmitting an operation instruction corresponding to an instruction with a gesture by the operator as a wireless signal.

The communication interface circuitry 21 is connected to the external device 40 through the network 100, etc., and performs data communication with the external device 40. The external device 40 is, for example, a database of a picture archiving and communication system (PACS) which is a system for managing various medical image data, a database of an electronic medical record system for managing electronic medical records to which medical images are added, etc. In addition, the external device 40 may, for example, be any medical image diagnostic apparatus other than the ultrasonic diagnostic apparatus 1 according to the present embodiment, such as an X-ray CT apparatus, a magnetic resonance imaging (MRI) apparatus, a nuclear medical diagnostic apparatus, and an X-ray diagnostic apparatus, etc. Any standards may be applied for communication with the external device 40. For example, digital imaging and communication in medicine (DICOM) may be applied.

The control circuitry 22 is a processor acting as a nerve center of the ultrasonic diagnostic apparatus 1, for example. The control circuitry 22 executes a control program stored in the internal storage 17 to realize a function corresponding to the program. Specifically, the control circuitry 22 executes a line delay data generation function 101.

By executing the line delay data generation function 101, the control circuitry 22 generates line delay data for two-dimensionally arranged elements. The line delay data and generation of the line delay data will be described in detail with reference to FIG. 6. The control circuitry 22 generates a delay time for each sub-array relating to the delay of the entire system (sub-array delay data), and transmits to the ultrasonic transmitting circuitry 11 the sub-array delay data as an analog signal.

The line delay data generation function 101 may be described as a control program, or may be implemented by hardware circuitry specific to each function included in the control circuitry 22 or the apparatus body 10.

The control circuitry 22 may be implemented by an ASIC (Application Specific Integrated Circuit) which includes hardware circuit specific to the function, a Field Programmable Gate Array (FPGA), a Complex Programmable Logic Device (CPLD), or a Simple Programmable Logic Device (SPLD).

Next, the configuration of the ultrasonic probe 30 according to the present embodiment will be explained with reference to the block diagram of FIG. 2.

The ultrasonic probe 30 includes a connector 200 (also referred to as POD), a cable 230, and a probe body 250 (also referred to as HEAD).

The connector 200 is a connector connected to the apparatus body 10, and includes a communication control circuit 201 and a storage 202. The probe body 250 includes a plurality of transmitting/receiving ICs 251 and a plurality of elements 252.

The communication control circuit 201 receives line delay data from the ultrasonic transmitting circuitry 11 of the apparatus body 10, and stores the line delay data in the storage 202. The communication control circuit 201 transmits the line delay data to the probe body 250 through the cable 230.

The storage 202 which is, for example, a memory, receives and stores line delay data.

The respective transmitting/receiving ICs 251 receive the line delay data from the communication control circuit 201, and driving signals from the ultrasonic transmitting circuitry 11. The respective transmitting/receiving ICs 251 set a delay amount of elements for each corresponding sub-array to which the respective transmitting/receiving ICs 251 control, based on the line delay data and the driving signal, and control transmission/reception of ultrasonic waves at a predetermined timing.

The delay amount is set to each of the plurality of elements 252 by the transmitting/receiving ICs 251, and ultrasonic waves generated based on the driving signals are transmitted to a living body P at timings corresponding to the respective delay amounts.

Once the ultrasonic probe 30 transmits ultrasonic waves to a living body P, the transmitted ultrasonic waves are sequentially reflected by the boundary showing discontinuity of the acoustic impedance of the living tissue of the living body P, and are received by the plurality of elements 252 as reflected waves. The amplitude of the received reflected waves depend on the difference in the acoustic impedance at the boundary showing discontinuity of the acoustic impedance that affects the reflection of ultrasonic waves. If the transmitted ultrasonic pulses are reflected in a bloodstream or on the surface of the cardiac wall, the frequency of the reflected waves are shifted depending on velocity components in the direction of transmitting ultrasonic waves in a moving object due to the Doppler effect. The ultrasonic probe 30 receives the reflected waves from the living body P, converts the reflected waves into electrical signals, and transmits the electrical signals to the apparatus body 10.

Next, the configuration of the transmitting/receiving ICs 251 will be explained with reference to the block diagram of FIG. 3.

The transmitting/receiving ICs 251 include an IC control circuit 301 and a plurality of sub-array units 350.

The IC control circuit 301 executes a delay setting function 302. By executing the delay setting function 302, the IC control circuit 301 calculates a delay amount for each element belonging to respective sub-arrays based on the line delay data acquired from the communication control circuit 201, and sets the delay amount for the respective sub-array units 350.

The respective sub-array units 350 receive driving signals from the ultrasonic transmitting circuitry 11, and receive the delay amount from the IC control circuit. The respective sub-array units 350 control the timing of ultrasonic transmission/reception of elements in an allocated sub-array based on the driving signals and the delay amount.

The sub-array units 350 will be explained in detail, with reference to the block diagram of FIG. 4.

Each of the sub-array units 350 includes an adding circuit 351 and a plurality of element transmitting/receiving circuits 352. The element transmitting/receiving circuit 352 is provided for each channel. The element transmitting/receiving circuit 352 includes a delay circuit 401, a transmitting amplifier circuit 402, a separation circuit 403, and a receiving amplifier circuit 404.

The adding circuit 351 adds receive signals in which delay processing is performed by the delay circuit 401.

The delay circuit 401 receives the delay amount from the IC control circuit 301, driving signals from the ultrasonic transmitting circuitry 11, and receive signals from the receiving amplifier circuit 404, and sets the delay amount relative to the transmit/receive signal.

The transmitting amplifier circuit 402 receives driving signals from the delay circuit 401, and amplifies the driving signals.

The separation circuit 403 separates the driving signals regarding transmission and echo signals received by elements.

The receiving amplifier circuit 404 receives echo signals from the separation circuit 403, and amplifies the echo signals.

(Setting Process of the Delay Time for Each Element)

The delay time setting for each element performed by the ultrasonic diagnostic apparatus according to the present embodiment will be explained. In the setting process, in the case where a two-dimensional array probe is used in which a plurality of elements are arranged in the first array direction and the second array direction, the delay data (line delay data) determined in element line units in each direction is transferred from the apparatus body 10 to the ultrasonic probe 30 during the blanking time. The ultrasonic probe 30 sets the delay time for each element by setting the delay amount for each element in the addition process during the same blanking time, by using the delay data received from the apparatus body 10 for each element line in each direction and the delay data for each sub-array. By this process, the setting of delay data for the large scale of two-dimensional array is established in a short time.

The outline of the setting process of delay time for each element will be explained with reference to FIGS. 5 and 6.

Figure 5:
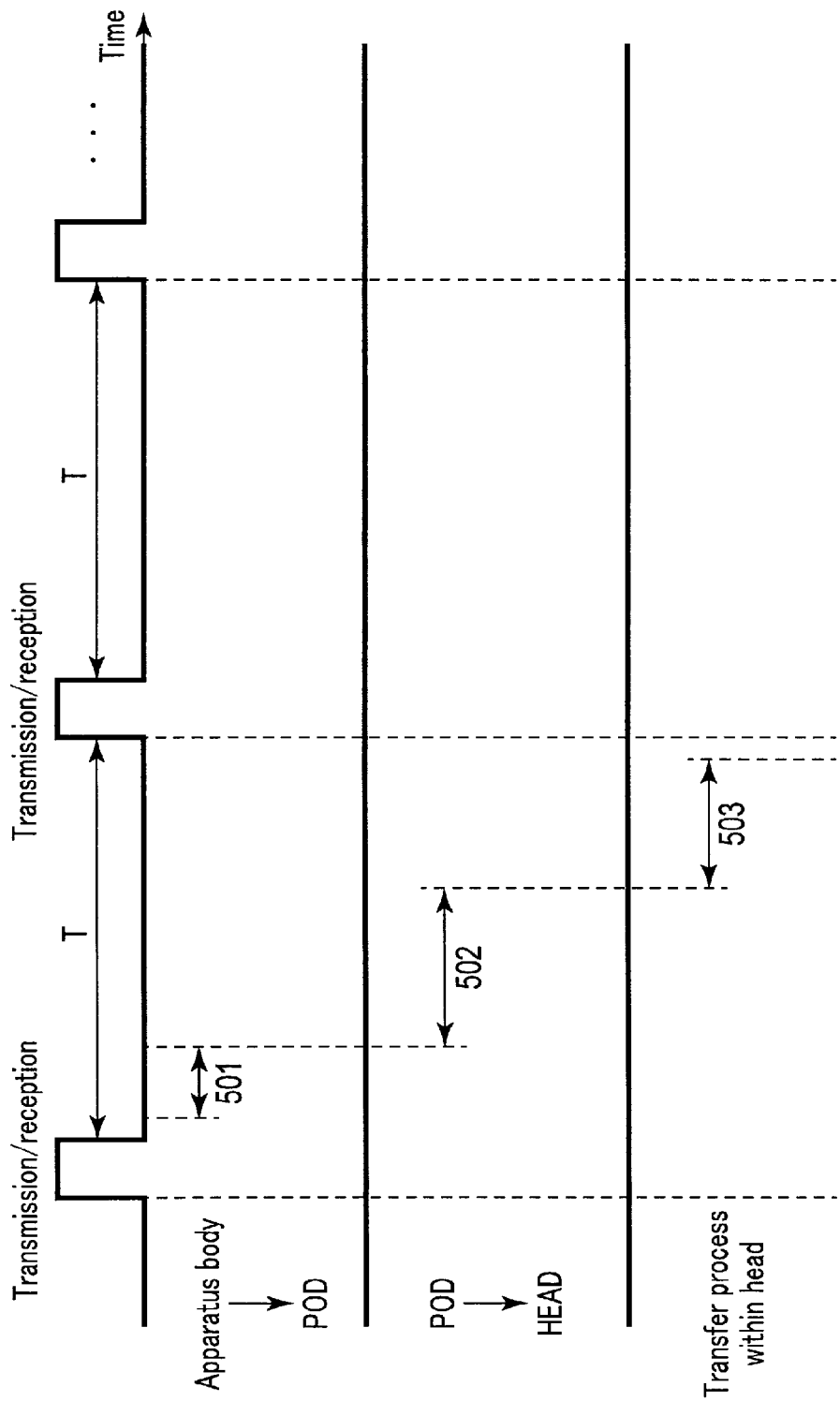
FIG. 5 is a conceptual diagram of blanking time.

FIG. 5 illustrates the blanking time and the timing of each process for setting the delay time performed during each blanking time. The timing chart at the top of FIG. 5 indicates the transmission/reception interval (pulse repetition interval; PRI) of ultrasonic waves of the ultrasonic diagnostic apparatus 1. The time T between a transmission/reception and a subsequent transmission/reception corresponds to a blanking time. The ultrasonic diagnostic apparatus 1 needs to complete a transfer process of the delay data from the apparatus body 10 directed to the ultrasonic probe 30 for the two-dimensional array (also referred to as data) which indicates subsequent transmission/reception of ultrasonic waves, and complete a setting process of delay time for each element in the ultrasonic probe 30, within each blanking time.

FIG. 5 indicates a transfer period from the apparatus body 10 to the ultrasonic probe 30 that includes a transfer period 501 in which transfer is performed from the apparatus body 10 to the connector (POD), and a transfer period 502 in which transfer is performed from the connector to the probe body (HEAD), and a transfer processing period 503 in the probe body 250 which corresponds to a setting process of a delay time for each element in the ultrasonic probe 30.

Figure 6:
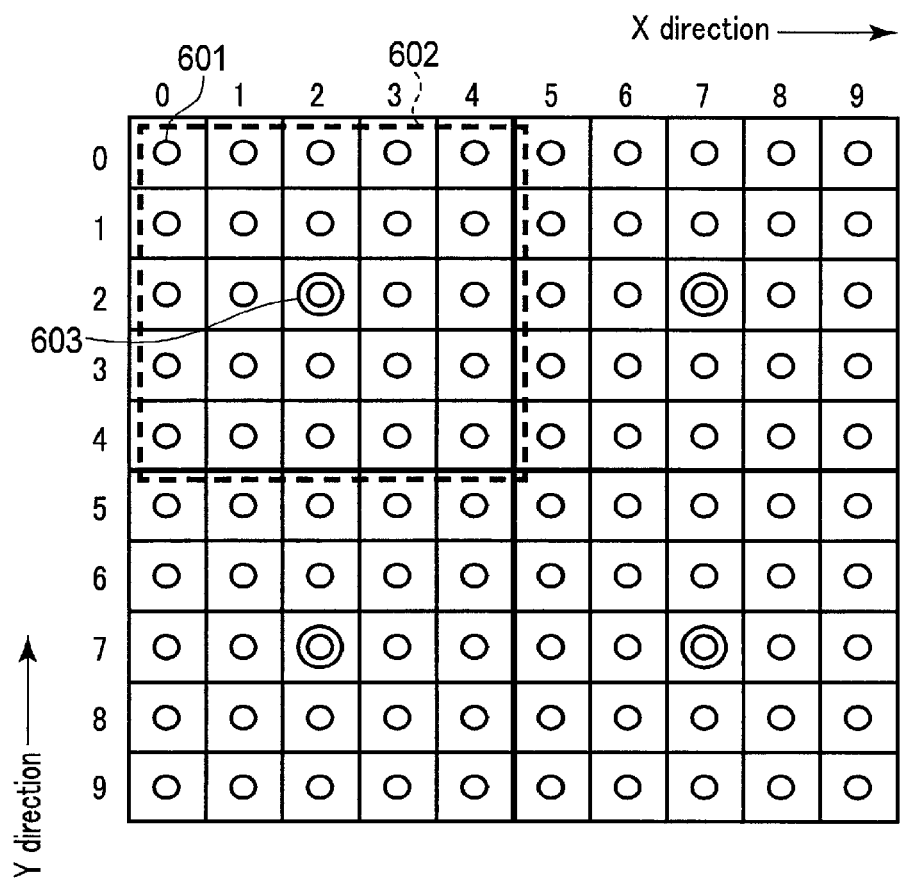
FIG. 6 is a conceptual diagram illustrating calculation of a delay amount of each element performed at the transmitting/receiving IC.

FIG. 6 illustrates the calculation method of line delay data in each direction, and sub-array delay data for each sub-array. In FIG. 6, each cell corresponds to an element position 601 of two-dimensionally arranged elements. To simplify the explanation, FIG. 6 illustrates 10×10 elements, i.e., 100 elements in total. An address out of 0 to 9 is allocated to each element in the X direction and the Y direction, and each element is defined by x and y coordinates. For example, the address of top left element is (0, 0), and the address of bottom right element is (9, 9).

A set of 5×5 elements is defined as a sub-array 602, and an element in the center of the sub-array 602 is defined as a sub-array position 603. That is, an example shown in FIG. 6 includes four sub-arrays 602.

To calculate the delay amount of each element corresponding to a focus point of the living body P, the coordinates of a focus point are defined as (xf, yf, zf), the coordinates of a sub-array position are defined as (xs, ys), and the coordinates of an element position are defined as (xe, ye). The sub-array delay data ds corresponding to a focus point is calculated in the control circuitry 22, based on equation (1).

$$ds = \sqrt{(xs-xf)^2 + (ys-yf)^2 + zf^2} - \sqrt{xf^2 + yf^2 + zf^2} \tag{1}$$

The line delay data dx in the X direction, and the line delay data dy in the Y direction corresponding to a focus point are calculated in the line delay data generation function 101, based on equation (2) and equation (3).

$$dx = \sqrt{(xe-xf)^2 + zf^2} - \sqrt{(xs-xf)^2 + xf^2} \tag{2}$$

$$dy = \sqrt{(ye-yf)^2 + zf^2} - \sqrt{(ys-yf)^2 + xf^2} \tag{3}$$

The line delay data dx is a delay amount determined for each line of the elements arranged along the Y direction, and the same delay amount is applied to elements within the same line. Similarly, the line delay data dy is a delay amount determined for each line of the elements arranged along the X direction.

In accordance with the above calculation, the same delay amount is applied to elements in the same line. For example, the same line delay data is applied to a line of x coordinate, "0", i.e., a line consisting of elements positioned in (0, 0) to (0, 9).

The calculation of each sub-array delay data ds relative to a focus point, each line delay data dx relative to the X direction, and each line delay data dy relative to the Y direction is performed and stored at a predetermined timing, before initiation of the ultrasonic transmission/reception. The line delay data generation function 101 transfers the line delay data dx relative to the X direction and the line delay data dy relative to the Y direction to be applied for the transmission to the connector 200 (POD) in the transfer period 501, and the communication control circuit 201 transfers the received line delay data dx relative to the X direction and line delay data dy relative to the Y direction to the probe body 250 (HEAD) in the transfer period 502 shown in FIG. 5.

The transmitting/receiving ICs 251 in the probe body 250 (HEAD) set the delay amount for each element in the sub-array by using a value obtained by adding the line delay data dx relative to the X direction and the line delay data dy relative to the Y direction, according to the address of each element, in the transfer processing period 503 in the probe body 250, shown in FIG. 5. The transmitting/receiving ICs 251 control transmission/reception of ultrasonic waves relative to elements 252 in accordance with the set delay time. For example, for an element position (1, 3) shown in FIG. 6, line delay data $dx_1$ of the second line in the X direction (the address in the X direction is 1) and line delay data $dy_3$ of the fourth line in the Y direction (the address in the Y direction is 3) are added, and a delay amount of an element in the intersection point (1, 3) is set. In the element transmitting/receiving circuit 352 that controls an element in the element position (1, 3), a delay is applied to driving signals from the apparatus body based on the calculated element delay amount, and ultrasonic waves are generated from the element during transmission. In reception process, the receive signals from the elements 252 are amplified by the receiving amplifier circuit 404, delay is applied to the receive signals based on the calculated delay amount, and the receive signals are output to the adding circuit 351. A system delay based on the sub-array delay ds is applied to an output of the adding circuit 351 at the ultrasonic receiving circuitry 12 of the apparatus body 10, and the addition process is applied to output receive signals.

The outline of the setting of the delay time according to the present embodiment is as explained above; however, the setting is not limited thereto. For example, the case where the sub-array delay setting for transmission is performed by the analog driving signals is assumed in the aforementioned example; however, it is possible that the sub-array delay data is transmitted to the ultrasonic probe 30 as a digital signal. The IC control circuit 301 may calculate the delay time of an element by using the sub-array delay data and the line delay data, and set the delay time for each sub-array unit 350.

Next, an example of a two-dimensional arrangement of elements assumed in the present embodiment will be explained with reference to FIG. 7.

Figure 7:
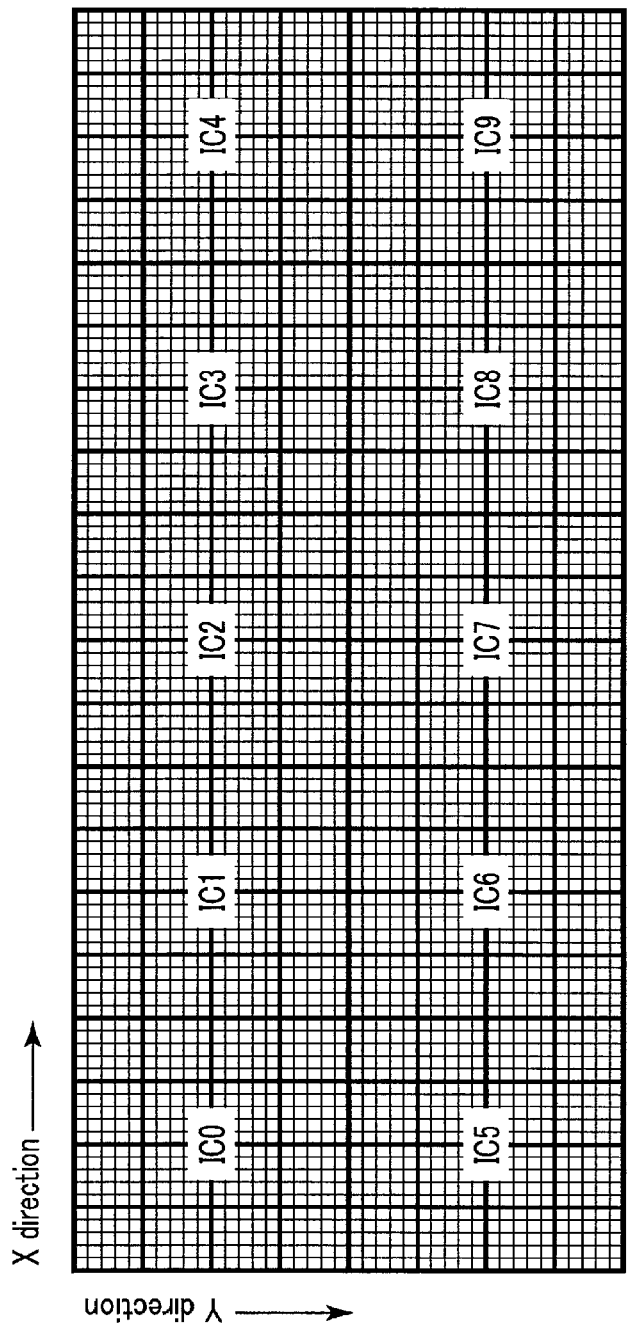
FIG. 7 shows an example of a two-dimensional arrangement of elements assumed in the present embodiment.

FIG. 7 indicates a two-dimensional array of elements in the ultrasonic probe that are recognized by the apparatus body 10. The case where 100 elements in the X direction and 40 elements in the Y direction are arranged, namely, 4000 elements in total, is assumed.

The sub-array size is 5×5 elements. One of the transmitting/receiving ICs 251 includes inputs for 20×20 elements, and controls 400 elements. One of the transmitting/receiving ICs 251 includes outputs for sub-arrays of 4×4 elements. Here, the case where 5 transmitting/receiving ICs 251 in the X direction and 2 transmitting/receiving ICs 251 in the Y direction are arranged, namely, 10 transmitting/receiving ICs 251 (IC0 to IC9) in total, is assumed. Each of the transmitting/receiving ICs includes a data receiving terminal and a data transmission terminal, and an output terminal of each of IC1 to IC9 is connected to an input terminal of the subsequent IC. Data is transferred to a subsequent IC by a bucket-brigade method between transmitting/receiving ICs. Specifically, data is successively transferred. For example, if data is input from IC0 to IC1, data input to IC1 in the previous clock is transferred to IC2.

The arrangement of the transmitting/receiving ICs 251 in FIG. 7 indicates the arrangement on an acoustic array. In the actual situation, there may be a case where the transmitting/receiving ICs are not arranged in a single plane, but are distributed in the vertical direction in the ultrasonic probe, and signals are derived from respective transmitting/receiving ICs by using a Flexible Printed Circuit (FPC).

Figure 8:
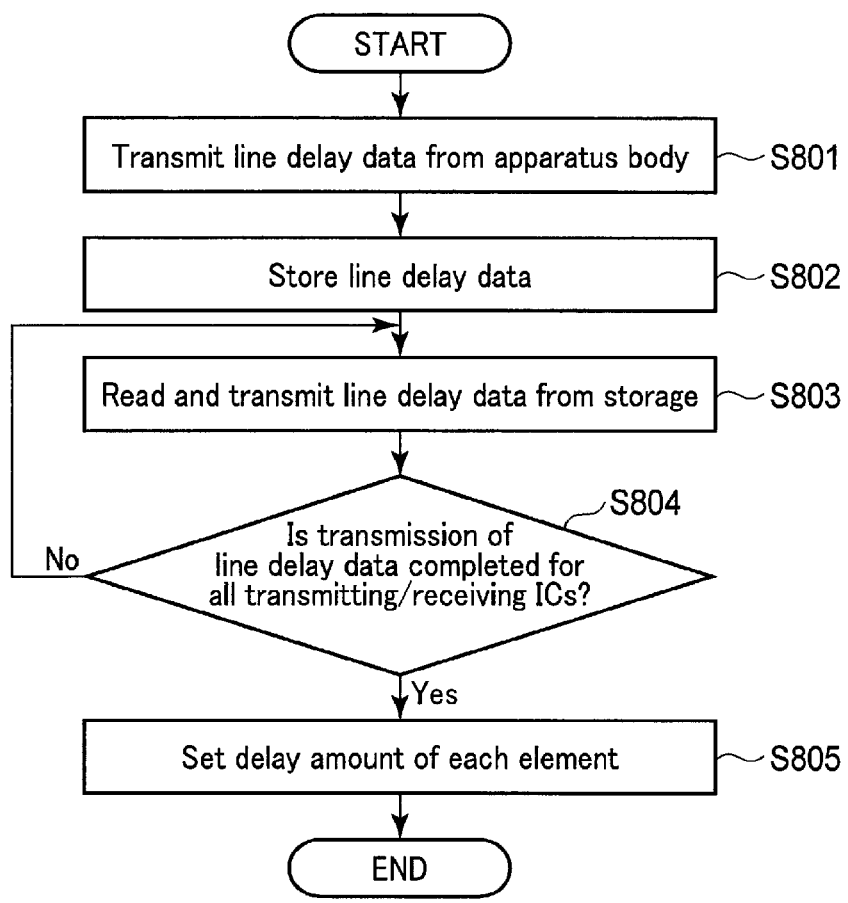
FIG. 8 is a flowchart indicating a delay amount setting process by the ultrasonic diagnostic apparatus according to the present embodiment.

Next, the delay amount setting process of the ultrasonic diagnostic apparatus according to the present embodiment will be explained with reference to the flowchart of FIG. 8. In the following explanation, it is assumed that the process is performed to the two-dimensional array shown in FIG. 7.

In step S801, the control circuitry 22 of the apparatus body 10 pre-calculates line delay data in the X direction and the Y direction (dx, dy) relative to 100×40 elements, and transmits the calculated line delay data to the communication control circuit 201 of the connector 200. The line delay data includes line delay data dx for 100 lines, i.e., dx [0:99], and line delay data dy for 40 lines, i.e., dy [0:39].

In step S802, the communication control circuit 201 stores the line delay data in the storage 202. The communication control circuit 201 re-arranges line delay data in an order of storing to the probe body 250 (an order of data transfer) for data transfer, and stores the rearranged line delay data. To save the memory space, the communication control circuit 201 may store the line delay data in an order of being received from the apparatus body 10 when storing data, and extract the line delay data from the storage 202 in an order of data transfer when transferring data.

In step S803, the communication control circuit 201 reads line delay data directed to "IC9" from the storage 202, and transmits the line delay data to the probe body so that line delay data is allocated in an order of data transfer to the transmission/reception arrays from the first destination "IC9". If line delay data is received at a data receiving terminal, receiving data of 1 clock prior to the current clock is output from a data transmission terminal in each transmitting/receiving IC.

In step S804, the communication control circuit 201 determines whether or not transmission of line delay data is completed for all of the transmitting/receiving ICs. This determination may be made based on whether an enable signal is received from the last destination "IC9" in the order of data transfer, for example. In this example, line delay data is transferred in an order from line delay data directed to "IC9" (40 items of line delay data represented by dx [80:99], dy [20:39]) to line delay data directed to "IC0" (dx [0:19], dy [0:19]). For example, once transfer of line delay data directed to "IC9" is completed, line delay data directed to "IC8" is transferred.

If line delay data transfer is completed, the process proceeds to step S805, and if line delay data transfer is not completed, the process returns to step S803, and the same process is repeated.

In step S805, the transmitting/receiving ICs 251 set the delay amount of each element based on the line delay data, as stated with reference to FIG. 6. The delay amount setting process of the ultrasonic diagnostic apparatus is completed by the aforementioned processing.

By adopting a plurality of data lanes, i.e., adopting a plurality of data receiving terminals and data transmission terminals, the line delay data can be transferred in parallel, thereby realizing high-speed data transfer.

Figure 9:
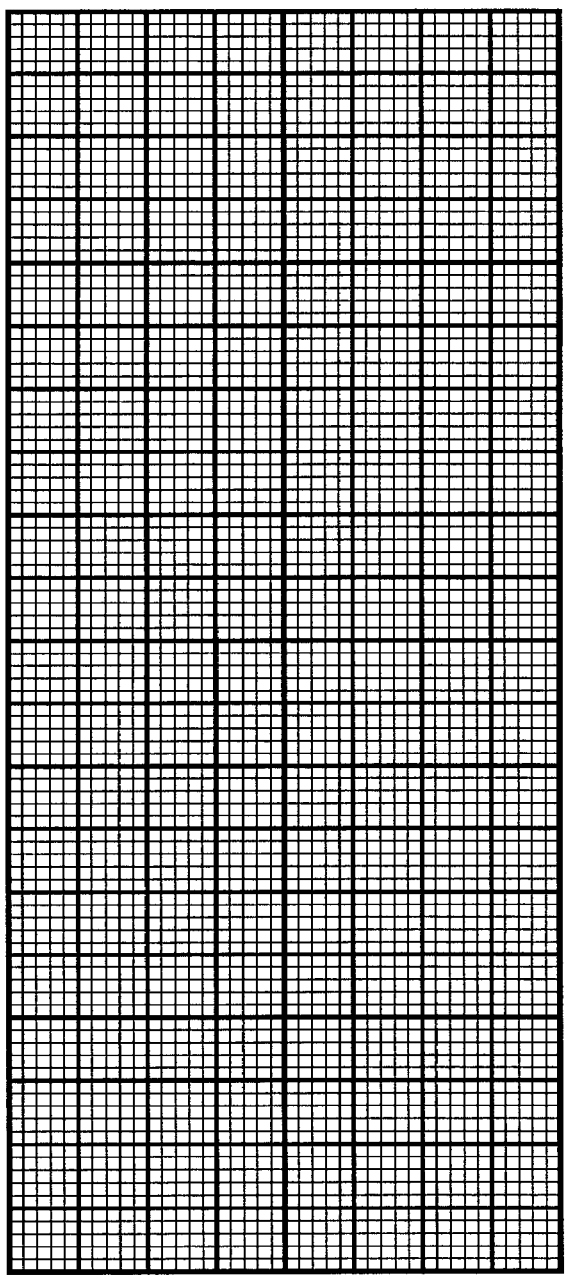
FIG. 9 illustrates a first comparison result between the conventional technique and the processing of the ultrasonic diagnostic apparatus according to the present embodiment.
Figure 9:
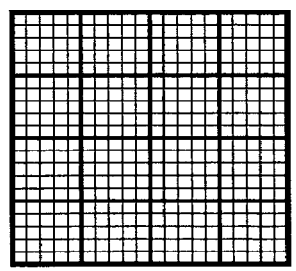

FIG. 9 illustrates a first comparison result between the conventional technique and the processing of the ultrasonic diagnostic apparatus according to the present embodiment.

FIG. 9 illustrates an array scale of elements controllable by the same data communication amount. FIG. 9 (*a*) is an array scale which is controllable by the conventional technique. In the conventional technique, the delay data is communicated for each element in a sub-array. Accordingly, 400 items of delay data are necessary for a sub-array of 20×20 elements, for example.

On the other hand, FIG. 9 (*b*) is an array scale controllable by the transfer method of the present embodiment. In the ultrasonic diagnostic apparatus according to the present embodiment, the delay amount of all the elements in a sub-array can be calculated by using 20 items of line delay data for each of the X direction and the Y direction. Accordingly, 40 (20+20) items of delay data are sufficient for setting the delay data for 400 elements. That is, in the case where the communication amount is the same as the conventional technique, the delay amount of elements in 10 sub-arrays can be communicated. Therefore, the controllable array scale is dramatically improved in comparison with the conventional technique.

FIG. 10 illustrates a second comparison result between the conventional technique and the processing of the ultrasonic diagnostic apparatus according to the present embodiment.

FIG. 10 (*a*) illustrates the sound pressure intensity of echo signals in the conventional technique in which the delay amount is calculated for each channel, and FIG. 10 (*b*) illustrates the sound pressure intensity of echo signals by the ultrasonic diagnostic apparatus according to the present embodiment. The ordinate represents an azimuth angle, and the abscissa represents an elevation angle.

In comparison between FIG. 10 (*a*) and FIG. 10 (*b*), FIG. 10 (*b*) shows that a grating lobe of 45 degrees is increased, but the amount of grating lobe is originally small, and thus has little effect. Accordingly, it can be read that the similar level of accuracy is maintained in the ultrasonic diagnostic apparatus according to the present embodiment in comparison with the conventional technique in which the delay amount is calculated for each channel.

FIG. 11 shows magnified views of the sound pressure intensity of main beams in FIG. 10.

FIG. 11 (*a*) indicates the results obtained in the conventional technique, and FIG. 11 (*b*) indicates the results obtained by the ultrasonic diagnostic apparatus according to the present embodiment. In comparison between FIG. 11 (*a*) and FIG. 11 (*b*), the sound pressure shows almost no loss, and there is almost no influence on the side lobe. Therefore, the delay amount setting method of the ultrasonic diagnostic apparatus according to the present embodiment exerts no influence in resolution in comparison with the conventional technique.

According to the first embodiment, the line delay data in two directions of the two-dimensional array is transferred to the ultrasonic probe, and the probe sets the delay amount of each element by applying a simple addition process, thereby setting the delay data for the large scale of two-dimensional array in a short time. That is, even if the array scale increases, transfer of two-dimensional array control data to the probe body can be completed within the blanking time.

With the ultrasonic diagnostic apparatus according to the present embodiment, as the array structure becomes larger, i.e., the channel number of system increases, the data communication amount reduction is further improved, which is one of the practical benefits of the present embodiment.

SECOND EMBODIMENT

A transmitting aperture can be set by applying the method of setting the delay amount based on line delay data.

The setting of transmitting aperture in the communication control circuit according to the second embodiment will be explained with reference to FIG. 12.

Figure 12:
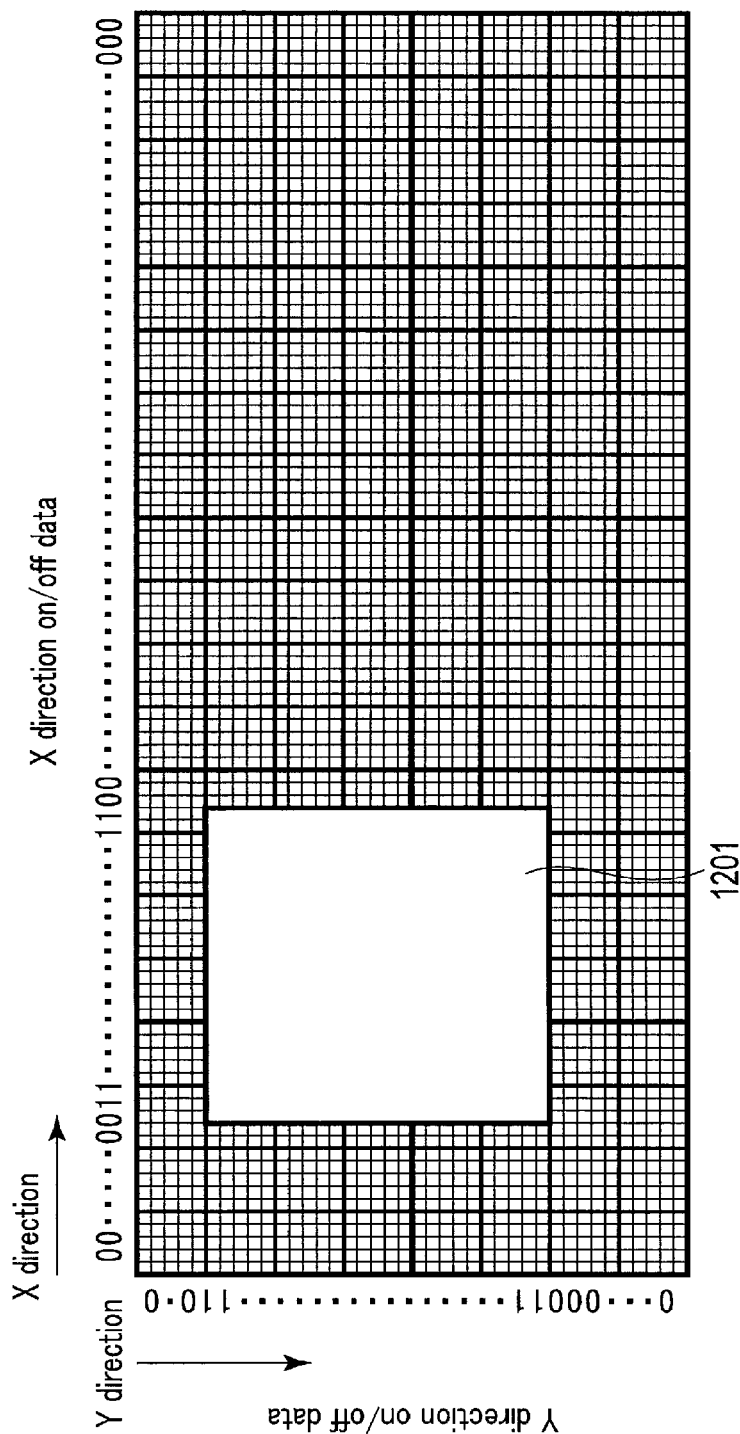
FIG. 12 illustrates an example of a setting of a transmitting aperture in a communication control circuit according to the second embodiment.

FIG. 12 illustrates the array structure similar to FIG. 7, and also illustrates a transmitting aperture 1201 that indicates an area of elements to be used for transmission.

The apparatus body 10 transmits to the communication control circuit 201 on/off data ax relating to ultrasonic transmission (first on/off data) for each line of elements along the Y direction, and on/off data ay relating to ultrasonic transmission data (second on/off data) for each line of elements along the X direction, in addition to the line delay data (dx, dy) according to the first embodiment. The on/off data (ax, ay) may be represented by 1 bit, for example. If a particular line is used for ultrasonic transmission, the particular line may be "1", and if the particular line is not used for ultrasonic transmission, the particular line may be "0". In addition to the line delay data dx [0:99] and dy [0:39], the first on/off data for 100 lines, i.e., ax [0:99], and the second on/off data for 40 lines, i.e., ay [0:39] are transmitted to the communication control circuit 201.

The communication control circuit 201 stores the line delay data and the on/off data (ax, ay) in the storage 202.

Similar to the first embodiment, the communication control circuit 201 sequentially transmits on/off data and line delay data from the data directed to IC9 to the transmitting/receiving ICs 251. Specifically, the on/off data and the line delay data are sequentially transmitted from ax [80:99], ay [20:39], dx [80:99], and dy [20:39] to ax [80:99], ay [20:39], dx [0:19], and dy [0:19].

The transmitting/receiving ICs 251 performs multiplication of the on/off data ax and the on/off data ay (bitwise AND operation), ax×ay, so that an element used for ultrasonic transmission is set. Specifically, an AND operation of the on/off data ax and the on/off data ay is performed, and only if the obtained value is "1", i.e., both of the on/off data ax and the on/off data ay are "1", is the corresponding element set to be used for ultrasonic transmission. By performing an AND operation to all elements in the two-dimensional array, the transmitting aperture 1201 can be obtained.

According to the aforementioned second embodiment, the on/off data in the X direction (azimuth direction) and the Y direction (elevation direction) is transmitted, and the ultrasonic probe body performs an AND operation. By this operation, data for setting the transmitting aperture for each channel can be transmitted to the ultrasonic probe in a short time, in comparison with the conventional technique.

In the above embodiments, the communication control circuit 201 and the storage 202 are included in the connector 200 connected to the apparatus body 10; however, the communication control circuit 201 and the storage 202 may be included in the apparatus body 10.

In addition, the elements included in the apparatus body 10, the communication control circuit 201, and the storage 202 according to the present embodiments may be included in the probe body 250. In this case, the probe body 250 may be connected to a display 50 (display, tablet terminal, smart phone, etc.) that displays an ultrasonic image via a USB (Universal Serial Bus), by wiring, or wirelessly.

(Modification of Embodiments)

In the above embodiments, it is assumed that line delay data dx and dy along the element arrangement directions are used; however, line delay data of diagonal lines may be further used to calculate a delay amount.

The line delay data generation function 101 may calculate line delay data (dr) for a line of elements placed on a diagonal line inclined upward right of the above line delay data, and line delay data (dl) for a line of elements placed on a diagonal line inclined downward left.

Four line delay data items will be explained with reference to FIG. 13, as a specific example. FIG. 13 shows one of the sub-arrays 602 shown in FIG. 6.

For convenience sake, line delay data of a diagonal line in which an element of address (0, 0) is placed is referred to as $dr_0$, and line delay data of a diagonal line in which elements of address (0, 1) and (1, 0) are placed is referred to as $dr_1$, for the line delay data dr. Similarly, line delay data of a diagonal line in which an element of address (0, 4) is placed is referred to as $dl_0$, and line delay data of a diagonal line in which elements of address (0, 3) and (1, 4) are placed is referred to as $dl_1$, for the line delay data dl.

The transmitting/receiving ICs 251 may set the delay amount for each element in a sub-array by using a value in which four line delay amount data items, dx, dy, dr, and dl are added according to the address of each element.

Specifically, it is assumed that the delay amount of an element of address (1, 3) is calculated. The transmitting/receiving ICs 251 may set the delay amount for each element in a sub-array by using a value obtained by adding line delay data $dx_1$, line delay data $dy_3$, line delay data of a diagonal line $dr_4$, and line delay data of a diagonal line $dl_3$.

As stated above, in the case where the delay amount is calculated by using line delay data in four directions, the delay amount can be highly accurately estimated, in comparison with the case using two line delay data items.

It is also possible that the delay amount of an element is calculated by adding two line delay data items which is line delay data dr and dl, without using line delay data dx or dy.

In the aforementioned embodiments, the case where a plurality of elements each formed in a rectangle shape are two-dimensionally arranged; however, the embodiments are not limited thereto.

For example, the case where a plurality of Micromachining Ultrasound Transducer (MUT) elements each formed in a hexagonal shape may be adopted.

The MUT elements may be Capacitive MUT (CMUT) elements (electrostatic capacitance transducer elements), or Piezoelectric MUT (PMUT) elements (piezoelectric transducer elements).

The calculation of the delay amount in the case where the hexagonal MUT elements are two-dimensionally arranged will be explained with reference to FIG. 14.

FIG. 14 illustrates an arrangement pattern of hexagonal MUT elements 1401. For convenience sake, the X direction and the Y direction are defined, and an identifier (ID) is allocated to each MUT element.

For example, in the case where the delay amount of an MUT element 1401 of ID "5" which is diagonally shaded is calculated, the transmitting/receiving ICs 251 may calculate the delay amount by adding line delay data in three directions. Specifically, the first line delay data is line delay data d1 relating to MUT elements 1401 (IDs=4, 5, 6, and 7) placed in the Y direction. The second line delay data is line delay data d2 relating to MUT elements 1401 (IDs=2, 5, and 8) placed in a line inclined upward right. The third line delay data is line delay data d3 relating to MUT elements 1401 (IDs=1, 5, and 9) placed in a line inclined upward left.

In the case where a plurality of MUT elements shown in FIG. 14 realize a function of one element shown in FIG. 6, the delay amount may be calculated by using the line delay data dx and dy (dx, dy, dr, and dl, if line delay data for four directions are adopted) according to the aforementioned embodiments, relative to the one element.

Furthermore, the functions described in connection with the above embodiments may be implemented, for example, by installing a program for executing the processing in a computer, such as a work station, etc., and expanding the program in a memory. The program that causes the computer to execute the processing can be stored and distributed by means of a storage medium, such as a magnetic disk (a hard disk, etc.), an optical disk (CD-ROM, DVD, etc.), and a semiconductor memory.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasonic diagnostic apparatus comprising:
an ultrasonic probe including a plurality of ultrasonic transducers two-dimensionally arranged along a first arrangement direction and a second arrangement direction; and
control circuitry configured to transmit first line delay data, second line delay data, and third line delay data to the ultrasonic probe, the first line delay data indicating a delay amount for each line of the ultrasonic transducers along the second arrangement direction, the second line delay data indicating a delay amount for each line of the ultrasonic transducers along the first arrangement direction, the third line delay data indicating a delay amount for diagonal lines of the ultrasonic transducers, wherein the ultrasonic probe further comprises:
a probe body that includes the plurality of ultrasonic transducers and setting circuitry configured to set a delay amount for each of the plurality of ultrasonic transducers, by using the transmitted first line delay data, second line delay data, and third line delay data; and
a connector that is connected to the probe body via a cable and includes the control circuitry,
the control circuitry is further configured to transmit to the setting circuitry first on/off data for each line of the ultrasonic transducers along the second arrangement direction, and second on/off data for each line of ultrasonic transducers along the first arrangement direction in a first period, the first on/off data indicating whether the ultrasonic transducers arranged in each line along the second arrangement direction are used for ultrasonic transmission or not, the second on/off data indicating whether or not the ultrasonic transducers arranged in each line along the first arrangement direction are used for ultrasonic transmission or not, and the setting circuitry is further configured to set ultrasonic transducers to be used for ultrasonic transmission based on both of the first on/off data in the second arrangement direction and the second on/off data in the first arrangement direction so as to set a transmitting aperture relating to the ultrasonic transmission of the ultrasonic probe in a second period different from the first period, wherein the setting circuitry sets a delay amount of each ultrasonic transducer by adding first line delay data, second line delay data, and third line delay data of a line corresponding to addresses of ultrasonic transducers belonging to a corresponding sub-array, and the ultrasonic probe transmits and receives ultrasonic waves from the plurality of ultrasonic transducers based on a sub-array delay relating to a system delay of the sub-array, and the delay amount.

2. The apparatus according to claim 1, wherein the setting circuitry sets the transmitting aperture by multiplying the first on/off data by the second on/off data, the first on/off data and the second on/off data relating to an address of each element belonging to a sub-array.

3. An ultrasonic diagnostic apparatus comprising:

an ultrasonic probe including a plurality of ultrasonic transducers two-dimensionally arranged along a first arrangement direction and a second arrangement direction; and transmit circuitry configured to transmit first line delay data, second line delay data, and third line delay data to the ultrasonic probe, the first line delay data indicating a delay amount for each line of the ultrasonic transducers along the second arrangement direction, the second line delay data indicating a delay amount for each line of the ultrasonic transducers along the first arrangement direction, the third line delay data indicating a delay amount for diagonal lines of the ultrasonic transducers, wherein the ultrasonic probe further comprises:

control circuitry configured to:

receive the first line delay data, the second line delay data, and the third line delay data from the transmit circuitry and re-arrange the received first line delay data, second line delay data and third line delay data in an order of being stored in the ultrasonic probe; and set a delay amount for each of the plurality of ultrasonic transducers, by using the first line delay data, second line delay data, and third line delay data stored in the ultrasonic probe, including adding the first line delay data, second line delay data, and third line delay data of a line corresponding to addresses of ultrasonic transducers belonging to a corresponding sub-array, wherein the ultrasonic probe transmits and receives ultrasonic waves from the plurality of ultrasonic transducers based on a sub-array delay relating to a system delay of the sub-array, and the delay amount.

4. An ultrasonic probe comprising:

a plurality of ultrasonic transducers two-dimensionally arranged along a first arrangement direction and a second arrangement direction; and setting circuitry configured to set a delay amount for each of the plurality of ultrasonic transducers by using first line delay data, second line delay data, and third line delay data, the first line delay data indicating a delay amount for each line of the ultrasonic transducers along the second arrangement direction, the second line delay data indicating a delay amount for each line of the ultrasonic transducers along the first arrangement direction, the third line delay data indicating a delay amount for diagonal lines of the ultrasonic transducers, the setting circuitry configured to set the delay amount of each ultrasonic transducer by adding the first line delay data, second line delay data, and third line delay data of a line corresponding to addresses of ultrasonic transducers belonging to a corresponding sub-array;

wherein the setting circuitry is further configured to:

receive first on/off data for each line of the ultrasonic transducers along the second arrangement direction, and second on/off data for each line of ultrasonic transducers along the first arrangement direction in a first period, the first on/off data indicating whether the ultrasonic transducers arranged in each line along the second arrangement direction are used for ultrasonic transmission or not, the second on/off data indicating whether the ultrasonic transducers arranged in each line along the first arrangement direction are used for ultrasonic transmission or not, and set ultrasonic transducers to be used for ultrasonic transmission based on both of the first on/off data in the second arrangement direction and the second on/off data in the first arrangement direction so as to set a transmitting aperture relating to the ultrasonic transmission of the ultrasonic probe in a second period different from the first period, wherein ultrasonic waves are transmitted and received from the plurality of ultrasonic transducers based on a sub-array delay relating to a system delay of the sub-array, and the delay amount.

5. The probe according to claim 4, further comprising:

a probe body that includes the plurality of ultrasonic transducers and the setting circuitry; and a connector that is connected to the probe body via a cable, wherein the connector comprises:

control circuitry configured to re-arrange the first line delay data, the second line delay data, and the third line delay data received from an ultrasonic diagnostic apparatus in an order of being stored in the probe body and transmit the rearranged first line delay data, second line delay data, and third line delay data to the setting circuitry of the probe body, and a memory configured to store the rearranged first line delay data, second line delay data, and third line delay data.

6. An ultrasonic diagnostic assistance method which controls an ultrasonic diagnostic apparatus, the ultrasonic diagnostic apparatus including an ultrasonic probe including a plurality of ultrasonic transducers two-dimensionally arranged along a first arrangement direction and a second arrangement direction, the method comprising:

transmitting first line delay data, second line delay data, and third line delay data to the ultrasonic probe, the first line delay data indicating a delay amount for each line of the ultrasonic transducers along the second arrangement direction, the second line delay data indicating a delay amount for each line of the ultrasonic transducers along the first arrangement direction, the third line delay data indicating a delay amount for diagonal lines of the ultrasonic transducers, and setting a delay amount for each of the plurality of ultrasonic transducers, by using the first line delay data, second line delay data, and third line delay data transmitted to the ultrasonic probe, including setting the delay amount of each ultrasonic transducer by adding the first line delay data, second line delay data, and third line delay data of a line corresponding to addresses of ultrasonic transducers belonging to a corresponding sub-array, transmitting to the ultrasonic probe first on/off data for each line of the ultrasonic transducers along the second arrangement direction, and second on/off data for each line of ultrasonic transducers along the first arrangement direction in a first period, the first on/off data indicating whether the ultrasonic transducers arranged in each line along the second arrangement direction are used for ultrasonic transmission or not, the second on/off data indicating whether the ultrasonic transducers arranged in each line along the first arrangement direction are used for ultrasonic transmission or not, setting ultrasonic transducers to be used for ultrasonic transmission based on both of the first on/off data in the second arrangement direction and the second on/off data in the first arrangement direction so as to set a transmitting aperture relating to the ultrasonic transmission of the ultrasonic probe in a second period different from the first period, and transmitting and receiving ultrasonic waves from the plurality of ultrasonic transducers of the ultrasonic probe based on a sub-array delay relating to a system delay of the sub-array, and the delay amount.

7. An ultrasonic diagnostic apparatus comprising:

an ultrasonic probe including a plurality of ultrasonic transducers two-dimensionally arranged along a first arrangement direction and a second arrangement direction; and control circuitry configured to transmit first line delay data, second line delay data, and third line delay data to the ultrasonic probe, the first line delay data indicating a delay amount for each line of the ultrasonic transducers along the second arrangement direction, the second line delay data indicating a delay amount for each line of the ultrasonic transducers along the first arrangement direction, the third line delay data indicating a delay amount for diagonal lines of the ultrasonic transducers, wherein the ultrasonic probe further comprises setting circuitry configured to set a delay amount for each of the plurality of ultrasonic transducers, by using the transmitted first line delay data, the transmitted second line delay data, and the transmitted third delay data, including setting the delay amount of each ultrasonic transducer by adding the first line delay data, second line delay data, and third line delay data of a line corresponding to addresses of ultrasonic transducers belonging to a corresponding sub-array, and wherein the ultrasonic probe transmits and receives ultrasonic waves from the plurality of ultrasonic transducers based on a sub-array delay relating to a system delay of the sub-array, and the delay amount.

* * * * *